US009211292B2

(12) United States Patent
Howard et al.

(10) Patent No.: US 9,211,292 B2
(45) Date of Patent: Dec. 15, 2015

(54) PREVENTING OR REDUCING DRUG ABUSE AND OVERDOSE EVENTS

(75) Inventors: William Wayne Howard, Morristown, NJ (US); Sheldon Kavesh, Whippany, NJ (US); Russell Francis Somma, Sparta, NJ (US)

(73) Assignee: ALITAIR PHARMACEUTICALS INC, Morristown, NJ (US)

( * ) Notice: Subject to any disclaimer, the term of this patent is extended or adjusted under 35 U.S.C. 154(b) by 0 days.

(21) Appl. No.: 13/385,322

(22) Filed: Feb. 14, 2012

(65) Prior Publication Data

US 2013/0034503 A1 Feb. 7, 2013

Related U.S. Application Data

(60) Provisional application No. 61/574,646, filed on Aug. 5, 2011.

(51) Int. Cl.
*A61K 31/485* (2006.01)
*A61K 31/37* (2006.01)

(52) U.S. Cl.
CPC ............... *A61K 31/485* (2013.01); *A61K 31/37* (2013.01)

(58) Field of Classification Search
CPC .................................................... A61K 31/485
See application file for complete search history.

(56) References Cited

U.S. PATENT DOCUMENTS

2007/0215511 A1* 9/2007 Mehta et al. .................. 206/531

* cited by examiner

*Primary Examiner* — Dennis J Parad
(74) *Attorney, Agent, or Firm* — Sheldon Kavesh

(57) ABSTRACT

A method and compositions for treating a patient that prevent or reduce drug abuse and overdose events.

20 Claims, 7 Drawing Sheets

Indicates an output
IR Resin Coating
IR Coating Solution
Water, HPMC, talc, triethyl citrate
Temperature
Time
Flow Rate
Spray Rate
Fluid Bed Processor
Transfer
Resinated Drug
Mesh Size
Speed
Delumping
Transfer
LOD
Assay
Release Rate
PSD
Density
Bulk Storage
Desiccant packs
Poly Bags
Fiber Drums
IR Coated Resin For Subsequent Forms

PREVENTING OR REDUCING DRUG ABUSE AND OVERDOSE EVENTS

CROSS-REFERENCE TO RELATED APPLICATIONS

This application claims the benefit of U.S. Provisional Application 61/574,646 filed Aug. 5, 2011. It is related to pending applications: Ser. No. 12/799,259 filed Apr. 21, 2010; Ser. No. 12/807,434 filed Sep. 3, 2010; and, Ser. No. 12/925,353 filed Oct. 20, 2010.

BACKGROUND OF THE INVENTION

1. Field of the Invention

The invention is a method and compositions for treating a patient that prevent or reduce drug abuse and overdose events.

2. Description of the Related Art

Many useful medications have serious safety issues related to overdose effects and abuse of the drugs by individuals. Drug overdose is characterized by negative unwanted effects such as paranoia, disorientation, stupor, nausea, depressed respiration, irregular heartbeats and even death. Although drug overdose may be intentional or unintentional, it is not the same as drug abuse. Drug abuse is a psychological phenomenon wherein individuals deliberately take doses of drugs, legal or illegal, to intentionally produce effects such as euphoria, hallucinations, exaggerated sense of well-being or invulnerability and other altered psychological states. Chronic drug abuse can create fundamental changes in brain structure and function.

Overdose of legal drugs is a very common problem causing more than one million emergency room visits per year and as many as 150,000 hospital admissions. Opiods, anti-depressants and tranquilizers are the leading agents in overdose events. Deaths from legal opioid analgesics in 2007 were 12,000: a far larger problem than deaths from drugs of abuse such as cocaine (6,000) and heroin (2,000). Moreover, unintentional drug overdose deaths have been increasing annually at a rate of about 13% per year.

Prescription and non-prescription drug abuse has also become a very serious public health problem. According to a recent report from the United States Department of Health and Human Services "In the United States in 2009, there were 7.0 million (2.8 percent) persons aged 12 or older who used prescription type psychotherapeutic drugs nonmedically in the past month." Another report by the CDC stated that prescription opioid use has increased 627% in the decade between 1997 and 2007. The report further noted that studies have shown that 100% of chronic opioid users develop dependence and that opioid treatment failure is most likely due to "rampant tolerance".

Drug tolerance and opioid tolerance specifically means that over time a patient or abuser needs to take increasing amounts of the drug to achieve the desired drug effect. Importantly, physical dependence and tolerance are widely believed to be two sides of the same coin. As a patient or drug user begins to exhibit symptoms of tolerance i.e. more and more of the drug is needed to produce the medical or abuse effect, the patient or abuser is also exhibiting a characteristic that is associated with tolerance, the development of drug dependency.

Dependency is often recognized by characteristic withdrawal symptoms that the person will exhibit when the drug effects begin to diminish. The symptoms can include an intense desire for more of the drug, convulsions, nausea, vomiting, irritability, paranoia, hallucinations and even death. Deliberate withdrawal as in detoxification often must be medically supervised to prevent harm to the patient from the withdrawal process.

Prescription and non-prescription drug abuse often involves taking the drug in amounts above those listed in the products recommended dosing schedule or more frequently than recommended in the dosing schedule.

There exists a class of drugs termed "Narrow Therapeutic Index (NTI)" drugs for which overdose events are an inherent hazard because of a narrow window between therapeutic and harmful dosage. NTI is defined in animal studies as the ratio of the lethal dose of a drug for 50% of the population (LD50) divided by the minimum effective dose for 50% of the population (ED50) i.e. LD50/ED50.

Such a definition is not possible in human studies and NTI for humans is defined as a ratio of a concentration of a drug required to produce toxic effect in 50% population (TE50) compared to the concentration of the drug required to produce required therapeutic effect in 50% (ED50) of the population i.e. TE50/ED50.

The FDA definition of NTI is found in 21 CFR 320.33(c) and is defined as follows:

a. There is less than a 2-fold difference in median lethal dose (LD50) and median effective dose (ED50) values, or b. There is less than a 2-fold difference in the minimum toxic concentrations and minimum effective concentrations in the blood, and c. Safe and effective use of the drug products require careful titration and patient monitoring.

Overdose and adverse events from NIT drugs is a significant public health issue. The CDC recently reported that adverse drug reactions resulted in over 700,000 patient visits annually to the emergency room. Most of the events were associated with a small number of narrow therapeutic index drugs. The CDC identified three drugs most commonly associated with emergency room/department visits included: warfarin, insulin and digoxin.

Patients 65 and older were twice as likely to experience an adverse reaction and seven times more likely to require hospitalization resulting from a reaction. The frequency of hospitalizations was similar to emergency department visits for motor vehicle occupant injuries according to the study.

The CDC reported that warfarin events are most often associated with bleeding events. The average length of stay for hospital-related bleeding events is six days at approximately $2,600 per day.

The U.S. Patent Office web site lists 7 patents, e.g., U.S. Pat. No. 7,375,083 B2, having the term "overdose" in its title, and 86 patents, e.g., U.S. Pat. No. 5,474,757 having the term "overdose" in its claims. There are 2,908 patents having the terms "overdose" and "drug", and 2,511 patents having the terms "overdose" and "pharmaceutical" anywhere within the patent. There are 203 patents having the term "drug abuse" in its claims, 20 patents having the term "drug abuse" in its title and 2,405 patents having the term "drug abuse" anywhere within the patent.

In a different area, 4,646 patents have the terms "ion exchange resin" and "drug" anywhere within the patent. 3,051 patents, e.g., U.S. Pat. No. 7,153,497 B2 have the term "ion exchange resin" in its claims. 219 patents use the terms "ion exchange resin" and "drug" and 105 patents use the terms "ion exchange resin" and "controlled release" in their claims. A review titled "Ion Exchange Resins in Drug Delivery", S. K. Bajpai et al., was published In "*Ion Exchange And Solvent Extraction. A series of Advances*", 18, P. 103-150, CRC Press, 2007.

U.S. Pat. No. 5,643,560 addressed overdose of psychotropic agents. It described use of a psychotropic agent-ion exchange complex admixed with an additional substance which affects the total amount of ions available to release the psychotropic agent from the complex.

Each of the prior patents represented an advance in the state of the art. However, there remains a long standing but unsatisfied need for an improved method for treating patients while reducing or preventing overdose events and abuse for a broad range of useful pharmaceutical products. While the implementing arts and elements have long been available, the method and compositions of this invention have not been suggested heretofore.

SUMMARY OF THE INVENTION

The new method and compositions of this invention use ion exchange resin technology to eliminate or to diminish the overdose hazard and adverse events if excessive quantities of the inventive product are accidently or intentionally ingested. They also provide a means of reducing drug abuse among patients or abusers who take the drug above the recommended dosing amounts or take the drug at more frequent intervals than recommended. The new methods employ compositions that are especially suited to situations wherein patients or abusers deliberately or unintentionally take more of the medicament at one time or in shorter intervals than is recommended or desirable.

In a first embodiment, the invention is a method of treating a patient that prevents or reduces drug abuse and overdose events, said method comprising: oral administration of a pharmaceutical composition comprising at least one drug bound to at least one exchange resin as a resinate, said ion exchange resins being selected from the group consisting of a cationic ion exchange resin and an anionic ion exchange resin, each said ion exchange resin being bound to at least one drug, wherein each said bound drug measured as the unbound state, is at less than about 75 percent of its saturation concentration in its resinate, said saturation concentration being defined as the larger of:

(a) the weight of drug per weight of washed and dried resinate after at least three hours of stirred aqueous resination reaction in a slurry of the drug in deionized water at a temperature in the range of 59 to 61° C. with the initial weight of drug being at least fourfold that of the weight of ion exchange resin present; and (b) the weight of drug per weight of washed and dried resinate after at least three hours of stirred aqueous resination reaction in a slurry of the drug with the initial weight of drug being at least fourfold that of the weight of ion exchange resin present, said aqueous resination reaction occurring at a temperature in the range of 59 to 61° C., and at a pH having a value within about ±1 unit of the $pK_a$ of the drug.

In a second embodiment, the invention is an oral dosage pharmaceutical composition useful for preventing or reducing overdose events and drug abuse comprising: at least one drug bound to at least one ion exchange resin as a resinate, said ion exchange resins being selected from the group consisting of a cationic ion exchange resin and an anionic ion exchange resin, each said ion exchange resin being bound to at least one drug, wherein each said bound drug, measured as the unbound state, is at less than about 75 percent of its saturation concentration in its resinate, said saturation concentration being defined as the larger of:

(a) the weight of drug per weight of washed and dried resinate after at least three hours of stirred aqueous resination reaction in a slurry of the drug in de-ionized water with the initial weight of drug being at least fourfold that of the weight of ion exchange resin present, said aqueous resination reaction occurring at a temperature in the range of 59 to 61° C.; and (b) the weight of drug per weight of washed and dried resinate after at least three hours of stirred aqueous resination reaction in a slurry of the drug with the initial weight of drug being at least fourfold that of the weight of ion exchange resin present, said aqueous resination reaction occurring at a temperature in the range of 59 to 61° C., and at a pH having a value within about ±1 unit of the $pK_a$ of the drug.

In a third embodiment, the invention is an oral dosage pharmaceutical composition as described above additionally comprising at least one unbound drug having a complementary therapeutic effect to any bound drug.

DETAILED DESCRIPTION OF THE INVENTION

Figure 1:
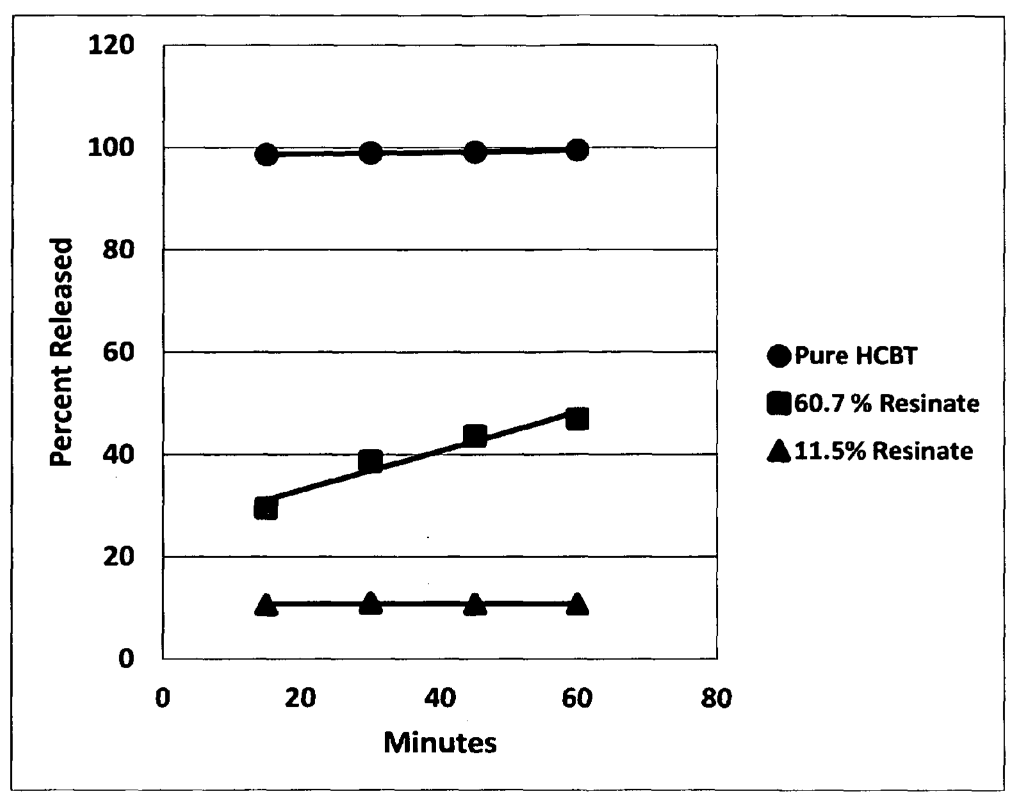
FIG. 1 is a plot of dissolution of pure hydrocodone bitartrate (HCBT) and HCBT/IRP69 resinates having 11.5%, and 60.5% HCBT loadings at 80 mg dosage under simulated empty stomach conditions.

In a first embodiment, the invention is a method of treating a patient that prevents or reduces drug abuse and overdose events, said method comprising: oral administration to a patient of a pharmaceutical composition comprising at least one drug bound to at least one ion exchange resin as a resinate, said ion exchange resins being selected from the group consisting of a cationic ion exchange resin and an anionic ion exchange resin, each said ion exchange resin being bound to at least one drug, wherein each said bound drug measured as the unbound state, is at less than about 75 percent of its saturation concentration in its resinate, said saturation concentration being defined as the greater of:

(a) the weight of drug per weight of washed and dried resinate after at least three hours of stirred aqueous resination reaction in a slurry of the drug in de-ionized water at a temperature in the range of 59 to 61° C. with the initial weight of drug being at least fourfold that of the weight of ion exchange resin present; and (b) the weight of drug per weight of washed and dried resinate after at least three hours of stirred aqueous resination reaction in a slurry of the drug with the initial weight of drug being at least fourfold that of the weight of ion exchange resin present, said aqueous resination reaction occurring at a temperature in the range of 59 to 61° C., and at a pH having a value within about ±1 unit of the $pK_a$ of the drug.

By "drug" is meant an active pharmaceutical agent (API) other than food articles that are intended to diagnose, cure, mitigate, treat or prevent disease in man or other animals or that are intended to affect the structure or any function of the body of man or other animals that are physiologically acceptable. The drug could be a combination of active pharmaceutical agents as well as a single agent.

By "overdose event" is meant an instance, where by ingestion of a quantity of a pharmaceutical active agent greater than the recommend dose, negative effects such as paranoia, disorientation, stupor, nausea, organ damage and even death occur.

By "prescription drug abuse" means taking a prescription medication that is not prescribed for the person taking it, or taking the prescription medication for reasons or in dosages other than as prescribed.

By "non-prescription drug abuse" means taking a non-prescription medication for reasons or in dosages other than as recommended on the package label.

The term "ion exchange resin" as used herein means any insoluble polymer that can act as an ion exchanger.

The term "resinate", or "drug/resin complex" means a complex formed between an active pharmaceutical agent and an ion exchange resin.

The terms "acid dissociation constant" and its symbolic representation "$pK_a$" as used herein are the negative of the logarithm of the dissociation constant of an acid or of a base (dimensionless). The $pK_a$ value of a drug may be measured by any of well known methods such as described in "Medium-Throughput Screening Of Pharmaceuticals By Pressure-Induced Capillary Electrophoresis", Jia et al., *Electrophoresis,* 22, 1112-1118 (2001) and "Measurement of Dissociation Constants ($pK_a$ Values) of Organic Compounds by Multiplexed Capillary Electrophoresis Using Aqueous and Cosolvent Buffers", Shalaeva et al., *J. of Pharmaceutical Sciences,* 97(7), 2581-2606 (2008)

The term "pH" is the negative of the logarithm of the dissociation constant of water in an aqueous solution (numerically equal to the negative logarithm of the hydrogen ion concentration in moles/liter).

The term "saturation concentration" means the weight of drug in a resinate, measured as the unbound state of the drug per weight of resinate after resination at specific conditions.

For the purposes of this invention, the saturation concentration of drug in a resinate is defined as the greater of:

(a) the weight of drug per weight of washed and dried resinate after at least three hours of stirred aqueous resination reaction in a slurry of the drug in de-ionized water at a temperature in the range of 59 to 61° C. with the initial weight of drug being at least fourfold that of the weight of ion exchange resin present; and (b) the weight of drug per weight of washed and dried resinate after at least three hours of stirred aqueous resination reaction in a slurry of the drug with the initial weight of drug being at least fourfold that of the weight of ion exchange resin present, said aqueous resination reaction occurring at a temperature in the range of 59 to 61° C., and at a pH having a value within about ±1 unit of the $pK_a$ of the drug.

The distinction between the (a) and (b) definitions of saturation concentration lies in the pH at which the saturation concentration is determined. While the art and science of resinate formation is not entirely predictable, it is expected that the saturation concentration will be greater when the resination reaction is conducted at a pH within about ±1 unit of the $pK_a$ of the drug.

The inventive method requires low drug loadings to provide additional resin binding capacity. Consequently, the same drug loading (grams of drug per gram of resinate), is expected to be a higher percentage of a saturation concentration according to the (a) definition of saturation concentration rather than the (b) definition. As drug loadings according to the invention must be less than 75% of a saturation concentration, any composition of the invention that meets the more stringent requirements of the (a) definition above, is also expected to be in compliance with the (b) definition.

Use of a slurry of the drug when determining saturation concentration assures that the concentration of the drug in solution will not be depleted during the resination reaction, and resinate formation will be maximized.

The $pK_a$ value of a drug may be known from the literature, or it may be determined by well known potentiometric, spectrophotometric and capillary electrophoresis methods such as noted above.

An ion-exchange resin is a naturally occurring material or a synthetically produced insoluble polymer matrix (or support structure) normally in the form of small (1-2 mm diameter) beads, usually white or yellowish, fabricated from an organic polymer substrate. The material has a highly developed structure of pores on the surface of which are sites which easily trap and release ions. The trapping of ions takes place only with simultaneous releasing of other ions; thus the process is called ion-exchange.

Ion exchange resins are classified as cation exchangers, that have positively charged mobile ions available for exchange, and anion exchangers, whose exchangeable ions are negatively charged. Both anion and cation resins are produced from the same basic organic polymers. They differ in the ionizable group attached to the hydrocarbon network. It is this functional group that determines the chemical behavior of the resin. Resins can be broadly classified as strong or weak acid cation exchangers or strong or weak base anion exchangers. When a drug substance is bound to an ion exchange resin, it is referred to as a resinate. Ion exchange is a reversible chemical reaction wherein an ion (an atom or molecule that has lost or gained an electron and thus acquired an electrical charge) from solution is exchanged for a similarly charged ion attached to an immobile solid particle.

A drug/resin complex (resinate) is achieved by an ionic bonding of a drug molecule to a resin bead. For cationic resinates, the drug molecule will only disassociate in the presence of an acidic environment and/or a strong electrolyte solution, e.g. NaCl, both of which are found in the stomach.

The inventive method requires cationic resins or anionic resins as part of the pharmaceutical formulation. The dosage forms can be either immediate release or sustained release formulations or both in one medicament.

Strong acid resins are so named because their chemical behavior is similar to strong acids. During the process of creating the resin polymer, a strong acid such as —$SO_3H$ is introduced into the resin. This sulfonic acid group is very highly ionizable and thus produces many ions available for the exchange process during drug resination.

In a weak acid resin the ionizable group introduced to the polymer is a carboxylic acid (—COOH) as opposed to the sulfonic acid group (—$SO_3H$) used in strong acid resins. These resins behave similarly to weak organic acids so are weakly dissociated i.e. have fewer ions available for exchange.

The acid dissociation constant, $pK_a$, is a quantitative measure of the extent of dissociation in solution. For an acid, the larger the value of $pK_a$, the smaller the extent of dissociation. For a strong acid such as —$SO_3H$, pKa is approximately 0. For the purposes of this invention, a strong acid resin is one having a pKa less than about 2. A weak acid such —COOH has a $pK_a$ in the range of 4.0 to 7.0. Strong acid resins useful in the invention include, for example, AMBERLITE™ IRP69, IRP69H, DOWEX™ 88, or DOWEX™ 50WX8.

IRP69 is thought to have a $pK_a$ value of less than 1 so is a strong acid resin. Weak acid resins useful in the invention include, for example, Amberlite IRP88, DOWEX MAC-3, but other weak acid ion exchange agents may be used.

Like strong acid resins, strong base resins are highly ionized and can be used over the entire pH range. It should be noted that strong base resins remain ionized even at high pH values. Strong base resins, anionic resins, are so named because their chemical behavior is similar to strong bases. During the process of creating the resin polymer, a strong base such as quaternary ammonium complex is introduced into the resin. This group is very highly ionizable and thus produces many ions available for the exchange process during drug resination. For the purposes of this invention, a strong base resin is one having a pKa of more than about 11. Useful strong base resins include DUOLITE™ 143 and the like. Useful weak base resins include Amberlite IRA67 and the like.

For resinates of cationic resins, the drug molecule will only disassociate in the presence of an acidic environment and/or a strong electrolyte solution e.g. NaCl, both of which are found in the stomach. When a cationic resinate is swallowed and enters the gastric environment, the reverse of the process described above begins. That is, the $H^+$ ions, $Na^+$ ions and others found in the stomach begin the ion exchange process again, releasing the drug into the gastric environment. The process continues until a state of equilibrium is reached between the drug ions trapped in the resin and the ions available in the gastric environment. When equilibrium is reached, no more of the drug ions will be released.

The factors that govern the concentration of the drug at equilibrium are complex and include the ionic strength of the resin, the size of the resin particles, the ionic strength of the pharmaceutical ingredient, the extent of the loading of the pharmaceutical agent on the resin, the number and strength of the ions in the releasing solution, the temperature of the solution and its pH.

Two other critical factors affect the quantity of the drug that is released at equilibrium. One is the volume of the fluid in the releasing environment and the second is the volume of resinate introduced into the releasing environment. If the volume of the releasing environment is held constant along with all other parameters associated with the environment including the drug and the resin loading characteristics, this leaves only one variable, the amount of drug resinate introduced into the releasing environment that will determine the equilibrium state of dissociation of the resin complex.

It is believed that as the weight of the resinate introduced into the releasing environment is increased, the proportion of the drug released will decrease in an exponential fashion, eventually reaching a plateau wherein the amount of drug released is a constant, independent of the total weight of the drug resin complex introduced.

If the drug resin complex is formulated in such a manner that the plateau level is below the toxic level, then overdose effects such as respiratory depression, cardiac arrhythmias or death will be avoided. Similarly, if the drug resin complex is formulated in such a manner that the plateau level is below the level that which produces euphoria, exaggerated sense of well-being or hallucinations are produced, drug abuse is discouraged. This effect will be especially useful for drug abusers who have developed a tolerance to the abused drug since they will need increasingly larger doses of the drug to achieve the desired effect. The present invention will significantly limit the release of doses of the drug beyond the labeled amount or dosing regimen thus preventing the drug abuser from achieving a drug high.

Improved methods to limit the release of a drug when a person has attempted drug abuse or has ingested a potential overdose are objects of the present invention.

The inventive methods employ a drug resinate created with a low to moderate loading of drug. Such a resinate has binding capacity left in the resin. This resin acts as a sink to absorb a portion of the ions in the gastric environment leaving fewer ions available to release a drug from its' resinate. The amount of binding capacity left in the resin can be varied to achieve the appropriate level of drug release and prevent or minimize occurrence of overdose events.

Preferably, a method of the invention employs a pharmaceutical composition in which each bound drug, measured as the unbound state, is at less than about 75 percent of its saturation concentration in its resinate.

More preferably, a method of the invention employs a pharmaceutical composition in which each bound drug, measured as the unbound state, is at less than about 50 percent of its saturation concentration in its resinate.

Still more preferably, a method of the invention employs a pharmaceutical composition in which each bound drug, measured as the unbound state, is at less than about 40 percent of its saturation concentration in its resinate.

Yet more preferably, a method of the invention employs a pharmaceutical composition in which each bound drug, measured as the unbound state, is at less than about 30 percent of its saturation concentration in its resinate.

Yet again more preferably, a method of the invention employs a pharmaceutical composition in which each bound drug, measured as the unbound state, is at less than about 20 percent of its saturation concentration in its resinate.

Most preferably, a method of the invention employs a pharmaceutical composition in which each bound drug, measured as the unbound state, is at less than about 10 percent, 5 percent or 1 percent of its saturation concentration in its resinate.

In a second embodiment, the invention is an oral dosage pharmaceutical composition useful for preventing or reducing drug abuse and overdose events comprising at least one drug bound to at least one ion exchange resin as a resinate, said ion exchange resins being selected from the group consisting of a cationic ion exchange resin and an anionic ion exchange resin, each said ion exchange resin being bound to at least one drug, wherein each said bound drug, measured as the unbound state, is at less than about 75 percent of its saturation concentration in its resinate, said saturation concentration being defined as the greater of:

(a) the weight of drug per weight of washed and dried resinate after at least three hours of stirred aqueous resination reaction in a slurry of the drug in de-ionized water at a temperature in the range of 59 to 61° C. with the initial weight of drug being at least fourfold that of the weight of ion exchange resin present; and (b) the weight of drug per weight of washed and dried resinate after at least three hours of stirred aqueous resination reaction in a slurry of the drug with the initial weight of drug being at least fourfold that of the weight of ion exchange resin present, said aqueous resination reaction occurring at a temperature in the range of 59 to 61° C., and at a pH having a value within about ±1 unit of the $pK_a$ of the drug.

A method and composition of the invention may additionally comprise one or more unbound drugs having complementary therapeutic effect to any bound drug. Preferably, unbound drugs have an $LD_{50}$ at least twice as high as any drug bound in a resinate.

It will be recognized that the overdose level of a drug is not well defined but the dose at 50% probability of lethal effects, the $LD_{50}$ of a drug, is measureable and is tabulated in standard sources. Hence, the ratios of $LD_{50}$ of drugs will be used as an indicator of relative overdose concentrations.

More preferably, unbound drugs in a pharmaceutical composition of the invention have an $LD_{50}$ four times as high as any drug bound in a resinate.

Yet more preferably, unbound drugs in a pharmaceutical composition of the invention have an $LD_{50}$ six times as high as any drug bound in a resinate.

Still more preferably, unbound drugs in a pharmaceutical composition of the invention have an $LD_{50}$ eight times as high as any drug bound in a resinate.

Most preferably, unbound drugs in a pharmaceutical composition of the invention have an $LD_{50}$ ten times as high as any drug bound in a resinate.

Preferably, each bound drug in a composition of the invention, measured as the unbound state, is less than about 50 percent of its saturation concentration in its resinate.

More preferably, each bound drug in a composition of the invention, measured as the unbound state, is less than about 40 percent of its saturation concentration in its resinate.

Yet more preferably, each bound drug in a composition of the invention, measured as the unbound state, is less than about 30 percent of its saturation concentration in its resinate.

Still more preferably, each bound drug in a composition of the invention, measured as the unbound state, is less than about 20 percent of its saturation concentration in its resinate.

Yet again more preferably, each bound drug in a composition of the invention, measured as the unbound state, is less than about 10 percent, 5 percent, or 1 percent of its saturation concentration in its resinate.

If the ion exchange resins in a composition of the invention are cationic resins, it is preferred that the unbound drugs have a pKa value less than 7. Also, if the ion exchange resins are anionic, it is preferred that the unbound drugs have a $pK_a$ value greater than 7. In this manner, the unbound drugs will not complete with the bound drugs for the ion exchange resins.

The method and compositions of the invention may employ a solid dosage form additionally contain a noxious tasting agent. By "noxious tasting agent" is meant an agent that, when released into the oral cavity is bitter, foul tasting, pepper like or any other agent that is otherwise safe and physiologically acceptable but has a very bad taste. Examples of suitable noxious tasting agents are:

Denatonium benzoate

Cayenne pepper

Capsaicin

The pharmaceutical oral dosage compositions employed in the invention can be formulated, for example, as a suspension, as a capsule or compressed tablet. Furthermore, such compositions may include a first, immediate release (IR) component, and a second, extended release (ER) component.

When the composition includes both such first and second components, by "immediate release" is meant that the release of the pharmacologically active agent from the first component is such that 80%, 85%, 90%, or even 95% of the ultimate extent of release from said component occurs within 45 minutes when dissolution is measured according to the USP 31 NF 26 section 711.

By "extended release" is meant that the pharmaceutically active agent is released from the second component at a controlled rate such that the formulation allows for a reduction in dosing frequency as compared to that presented by a conventional dosage form.

Pharmaceutically Active Agents

Examples of drugs for which the method and compositions of the invention are applicable include among others:

A: Anti-tussives, e.g., benzonatate, caramiphen edisylate, chlophedianol, codeine, dextromethorphan hydrobromide, hydrocodone, levopropoxyphene, morphine codeine, ethylmorphine, dihydrocodeine, benzylmorphine, laudanum, dihydroisocodeine, nicocodeine, nicodicodeine, hydrocodone, hydromorphone, acetyldihydrocodeine, thebacon, diamorphine (heroin), acetylmorphone, noscapine, and pholcodine.

B: Narcotic analgesics, e.g., codeine, oxycodone, hydrocodone, diamorphine, pethidine, morphine, oxymorphone, nalorphine, naloxone, naltrexone, opium, hydromorphone, nicomorphine, dihydrocodeine, and papavereturn.

C: Decongestants, e.g., pseudoephedrine hydrochloride, phenylephrine bitartrate, and pseudoephedrine sulfate.

D: Non-steroidal anti-inflammatory drugs, e.g., aspirin, magnesium salicylate, diclofenac, etodolac, indometacin, nabumetone, sulindac, tolmetin, ibuprofen, ketoprofen, mefenamic acid, meclofenamic acid, phenylbutazone, piroxicam, meloxicam, celecoxib, parecoxib, rofecoxib, valdecoxib, and naproxen sodium.

E: Anti-emetic drugs, e.g., dolasetron, granisetron, ondansetron, tropisetron, palonosetron, mirtazapine, metoclopramide, cyclizine, diphenhydramine, dimenhydrinate, meclizine, promethazine, and hydroxyzine.

F: Anti-histamines, e.g., diphenhydramine, loratadine, desloratadine, meclizine, fexofenadine, pheniramine, cetirizine, promethazine, and chlorpheniramine.

G: Proton pump inhibitors (PPI), e.g., omeprazole, esomeprazole, pantoprazole, lansoprazole, and rabeprazole.

H: H2 Antagonists, e.g., cimetidine, ranitidine, and famotidine.

I: Anti-depressants, e.g., citalopram, escitalopram, fluoxetine, fluvoxamine, paroxetine, sertraline, desvenlafaxine, duloxetine, milnacipran, venlafaxine, atomoxetine, mazindol, reboxetine, viloxazine, amitriptyline, clomipramine, doxepin, imipramine, trimipramine, desipramine, nortriptyline, protriptyline, moclobemide, phenelzine, and selegiline.

J: Tranquilizers, e.g., amobarbital, pentobarbital, secobarbital, phenobarbital, clonazepam, diazepam, estazolam, flunitrazepam, lorazepam, midazolam, nitrazepam, oxazepam, triazolam, temazepam, chlordiazepoxide, and alprazolam.

K: Anti-convulsants, e.g., felbamate, carbamazepine, oxcarbazepine, vigabatrin, progabide, tiagabine, topiramate, gabapentin, pregabalin, ethotoin, valproic acid, and phenytoin.

L: Hypnotics, e.g., zolpidem, zaleplon, zopiclone, and eszopiclone.

M: Muscle relaxants, e.g., methocarbamol, carisoprodol, chlorzoxazone, cyclobenzaprine, gabapentin, metaxalone, and orphenadrine.

N: Anti-psychotics, e.g., haloperidol, droperidol, chlorpromazine, fluphenazine, perphenazine, prochlorperazine, thioridazine, trifluoperazine, mesoridazine, promazine, triflupromazine, levomepromazine, methotrimeprazine, pimozide, chlorprothixene, flupenthixol, thiothixene, zuclopenthixol, clozapine, olanzapine, risperidone, quetiapine, ziprasidone, amisulpride, asenapine, and paliperidone.

O: Anti-microbials, e.g., EDTA, zinc compounds, triclosan, domiphen, cetyl pyridium chloride, domiphen bromide, fluorides, alexidine, and octenidine.

P: Anti-diarrheals, e.g., bismuth subsalicylate and loperamide.

R: CNS stimulants, e.g., caffeine, cocaine, and amphetamines.

S: Attention Deficit and Hyperactivity Disorder drugs, e.g., methylphenidate, dextroamphetamine sulfate, amphetamine, and atomoxetine hydrochloride.

T. Analgesics, e.g. acetaminophen, aspirin

U. Narrow Therapeutic Index (NTI) drugs

The FDA lists the following drugs as having a narrow therapeutic index:

Aminophylline
Carbamazepine
Clindamycin
Clonidine
Digoxin
Disopyramide
Dyphylline
Guanethidine
Isoetharine mesylate
Isoproterenol
Levoxyine
Lithium Carbonate
Metaporterenol
Minoxidil
Oxytriphylline
Phenytoin
Prazosin
Primidone
Procainamide
Quinidine gluconate
Theophylline
Valproic Acid
Warfarin sodium The inventive method is also intended for delivering combinations of pharmaceutically active compounds. Examples of such combinations among others are:

A: the drug and an antihistamine
B: the drug and a decongestant
C: the drug and an analgesic
D: the drug and an NSAID
E: the drug and an antihistamine and a decongestant
F: the drug and an antihistamine and an analgesic
G: the drug and an antihistamine and an NSAID
H: the drug and an antihistamine and a decongestant and an analgesic.

Preferably, the pharmaceutical agents act in therapeutically complementary ways, as in a combination of an antihistamine, a decongestant and an analgesic.

Oral Dosage Delivery Systems

Delivery systems employable in the method of the invention include suspensions, compressed tablets, capsules, granules/multi-particle systems, pellets as well as granules/multi-particle systems, pellets filled into capsules and the like.

EXAMPLES

The following examples are presented to provide a more complete understanding of the invention. The specific techniques, conditions, materials, proportions and reported data set forth to illustrate the principles of the invention are exemplary and should not be construed as limiting the scope of the invention.

Each of the solid oral dosage form compositions of the examples below is useful for oral administration as well as to prevent or reduce overdose or abuse of the drug

Example 1

A. Constituents

AMBERLITE™ IRP69 (a strong acid resin from Dow) was selected as the ion-exchange resin for this example having the structure shown below. The AMERLITE™ IRP69 was screened on a 270 Standard US Sieve to remove particles smaller than about 53 micrometers.

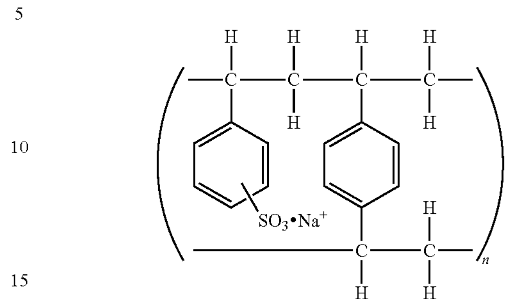

Hydrocodone bitartrate (hereinafter "HCBT") from Sigma-Aldrich Inc. was selected as a drug for this example having the molecular structure shown below.

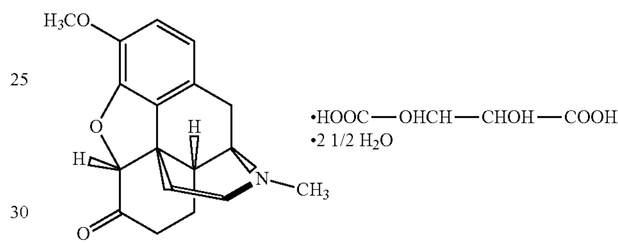

B. Saturation Concentration 12 grams of HCBT was dissolved at 60° C. in 100 grams of de-ionized water at the solubility limit of the HCBT. 1.00 grams of the sieved IRP 69 was added to the HCBT solution (12:1 drug to resin ratio). The mixture was agitated for four hours. At the end of this time, the mixture was filtered and the filter cake was washed three times by percolating with water. The filter cake was vacuum dried at 60° C. and forced through an 80 mesh screen to break up agglomerates.

The combined filtrate and wash waters were analyzed for residual HCBT and the loading of HCBT on the IRP69 resin was calculated by difference from the initial charge. It was found that the drug loading in the dry resinate was 89.9% (0.899 g HCBT/g resinate).

As the above procedure did not use a slurry of HCBT (excess HCBT beyond the solubility limit), it is believed that the saturation concentration of HCBT in IRP69 as defined herein was equal to or greater than 0.899 grams HCBT per gram of IRP69. Hence, HCBT compositions of the invention must have loadings of less than 0.75×0.899 g HCBT/g resinate=0.674 g HCBT/g resinate.

B. Resinates of the Invention 1.04 grams of HCBT were dissolved in 20.9 grams of de-ionized water at room temperature. (Note: the solubility of HCBT in water is 62 mg/ml Ref. Sigma Aldrich, temperature about 23° C.). 1.22 grams of the sieved IRP 69 was added to the HCBT solution. The mixture was agitated for three hours. At the end of this time, the mixture was filtered and the filter cake was washed three times by percolating with water. The filter cake was vacuum dried at 60° C. and forced through an 80 mesh screen to break up agglomerates.

The combined filtrate and wash waters were analyzed for residual HCBT and the loading of HCBT on the IRP69 resin was calculated by difference from the initial charge. It was found that the drug loading in the dry resinate was 60.7% (0.607 g HCBT/g resinate). This drug loading in proportion to the saturation concentration was 60.7%/89.9%=67.5%, and hence less than 75% of the saturation concentration of HCBT in IRP69.

A second batch of resinate was prepared using 39.1 g of deionized water, 1.96 g of HCBT and 17.4 g of IRP69 and the same procedure. The drug loading in the dry resinate was 11.5% (0.115 g HCBT/g resinate). This drug loading in proportion to the saturation concentration was 11.5%/89.9%=12.8%, and hence much less than 75% of the saturation concentration of HCBT in IRP69.

C. Dissolution Testing of Resinates and Pure HCBT

Characterization of the dissolution of the above resinates and pure HCBT in the human digestive system was simulated in two stages using the procedure described in USP 31 NF26 using Apparatus 2 (paddles). The resinate or pure HCBT was weighed to determine the dose to be tested. The resinate or pure HCBT powder was added directly to the vessel for dissolution testing without the use of a capsule or tablet and its associated excipients. The conditions in the first stage to simulate dissolution in an empty stomach were as follows:

Medium: 0.1N HCl

Volume: 250 ml

Temperature: 37° C.

RPM: 50

The above resinate of the invention having an 11.5% HCBT loading was tested at dosages of 10 mg, 40 mg and 80 mg HCBT. The resinate of the invention having 60.7% HCBT loading was tested at dosages of 10 and 80 mg HCBT. Pure HCBT was tested only at 80 mg dosage. A given dose was placed in the dissolution apparatus and stirred for a given length of time. At the end of that time, the quantity of HCBT released was determined by high pressure liquid chromatography.

The dissolution data for the pure HCBT, the two resinates, the three doses and four dissolution times are shown below in Tables I and II and are plotted in FIGS. 1 and 2.

TABLE I

| | HCBT Released, mg | | | | | |
|---|---|---|---|---|---|---|
| | 11.5% HCBT Resinate | | | 60.7% HCBT Resinate | | Pure HCBT |
| Time, min | 10 mg dose | 40 mg dose | 80 mg dose | 10 mg dose | 80 mg dose | 80 mg dose |
| 15 | 2.3 | 6.1 | 10.6 | 5.1 | 29.5 | 78.8 |
| 30 | 3.6 | 7.0 | 11.0 | 6.9 | 38.7 | 79.2 |
| 45 | 4.0 | 7.2 | 10.8 | 7.7 | 43.7 | 79.4 |
| 60 | 4.3 | 8.04 | 10.8 | 8.1 | 47.0 | 79.6 |

TABLE II

| | HCBT Released, Percent of Original Dose | | | | | |
|---|---|---|---|---|---|---|
| | 11.5% HCBT Resinate | | | 60.7% HCBT Resinate | | Pure HCBT |
| Time, min | 10 mg dose | 40 mg dose | 80 mg dose | 10 mg dose | 80 mg dose | 80 mg dose |
| 15 | 22.7 | 15.3 | 13.2 | 50.5 | 36.9 | 98.6 |
| 30 | 35.7 | 17.4 | 13.8 | 69.1 | 48.4 | 99.0 |
| 45 | 40 | 18.1 | 13.5 | 76.9 | 54.6 | 99.2 |
| 60 | 43.4 | 20.1 | 13.5 | 80.8 | 58.7 | 99.5 |

It will be seen that as the dosage increased, the absolute amount of dissolution did not increase proportionately. For the 11.5% resinate, increasing the dose from 10 mg to 80 mg, an eight fold increase, increased HCBT release from 4.3 mg to 10.8 mg, only a 2.5 fold increase. Consequently, there was more than a three-fold decrease in the percentage of the original dose that was released. This would serve as a protection against overdosing or abuse by a patient. Further, the lower the drug loading of the resinate (11.5% vrs. 60.7%), the greater was the protective decrease in proportion of release with increase dose.

Referring to FIG. 1, the data show that an 80 mg dosage in powder form of pure HCBT released essentially all of the drug and would likely cause a serious adverse event or death if taken by a human.

In comparison, the 11.5% HCBT resinate of the invention in 80 mg dosage form released only 10.8 mg of HCBT: an amount that would likely be safe if a human had take the drug with this formulation.

The 60.7% HCBT resinate released an intermediate 47% of the drug, showing that the release may be easily regulated from about half to about 10%.

Figure 2:
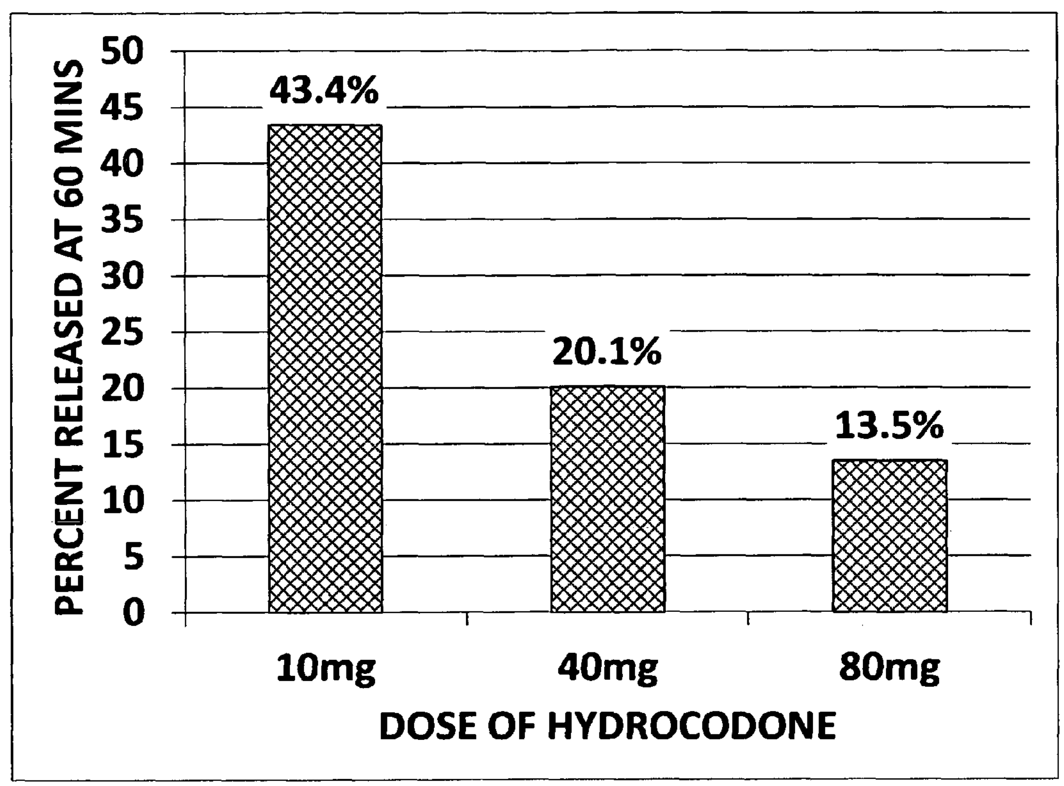
FIG. 2 is a bar chart showing of dissolution of 11.5% HCBT/IRP69 resinates at 10, 40 and 80 mg doses under simulated empty stomach conditions.

FIG. 2 shows a comparison of three dosages of HCBT for a constant 11.5% loading. The data shows that the proportion of drug release is not a constant fraction of the total amount of drug in the formulation, but rather is a decreasing function that may plateau at about 13%.

It will be seen that the inventive formulations provide for adequate release at low doses appropriate for clinical use, but at high doses, as in overdose or abuse, release is strongly limited and excessive amounts are not released.

A second stage of testing was to simulate dissolution of an inventive composition in the lower digestive system of a patient. The conditions and methods were the same as described above except that the pH of the water was 6.8 and the test ran for 12 hours. Only the 11.5% HCBT/IRP69 resinate at 80 mg dose was so tested.

Figure 3:
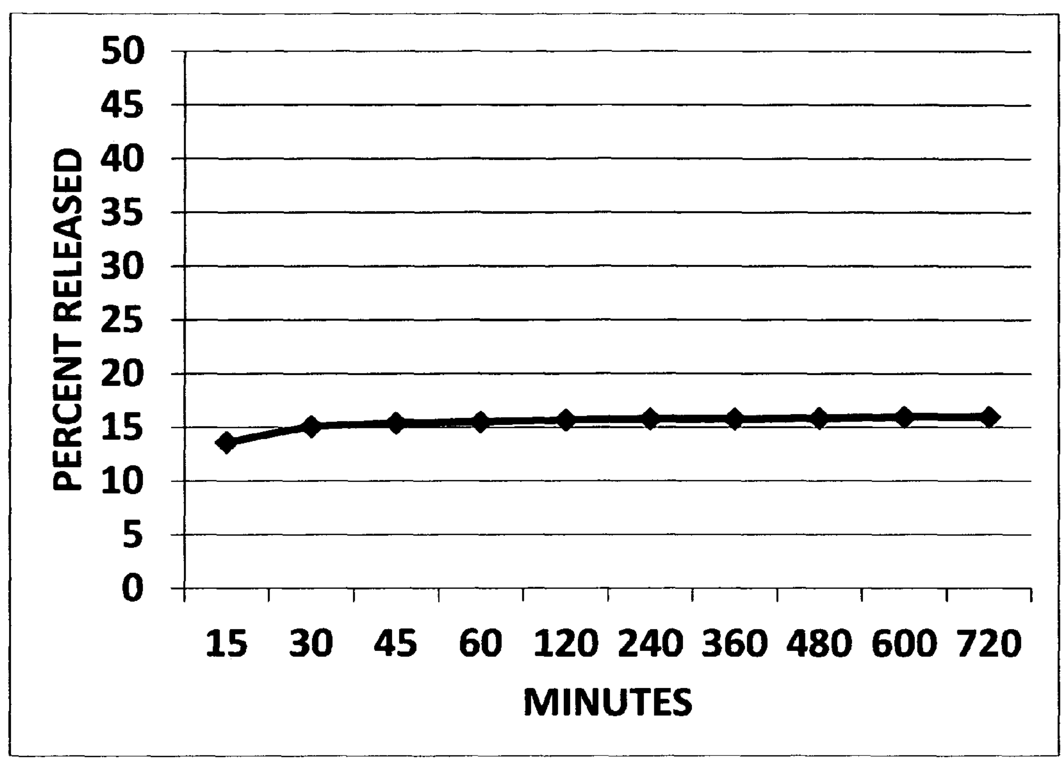
FIG. 3 is a plot of dissolution of an 11.5% HCBT/IRP69 resinate, 80 mg dose at pH 6.8 in simulated lower digestive conditions.

The dissolution data are presented below in Table III and are plotted in FIG. 3.

TABLE III

| | 11.5% HCBT Resinate, 80 mg dose | |
|---|---|---|
| Time, min. | HCBT Release, mg | % Release |
| 0 | 0 | 0 |
| 15 | 10.84 | 13.55 |
| 30 | 12.104 | 15.13 |
| 45 | 12.304 | 15.38 |
| 60 | 12.368 | 15.46 |
| 120 | 12.552 | 15.69 |
| 240 | 12.6 | 15.75 |
| 360 | 12.64 | 15.8 |

TABLE III-continued

| 11.5% HCBT Resinate, 80 mg dose | | |
|---|---|---|
| Time, min. | HCBT Release, mg | % Release |
| 480 | 12.68 | 15.85 |
| 600 | 12.76 | 15.95 |
| 720 | 12.8 | 16 |

It will be seen that release in the lower digestive system of a patient would be no greater than release in the stomach.

Example 2

An Immediate Release Resinate Intermediate for Hard Gelatin Capsules

Figure 4:
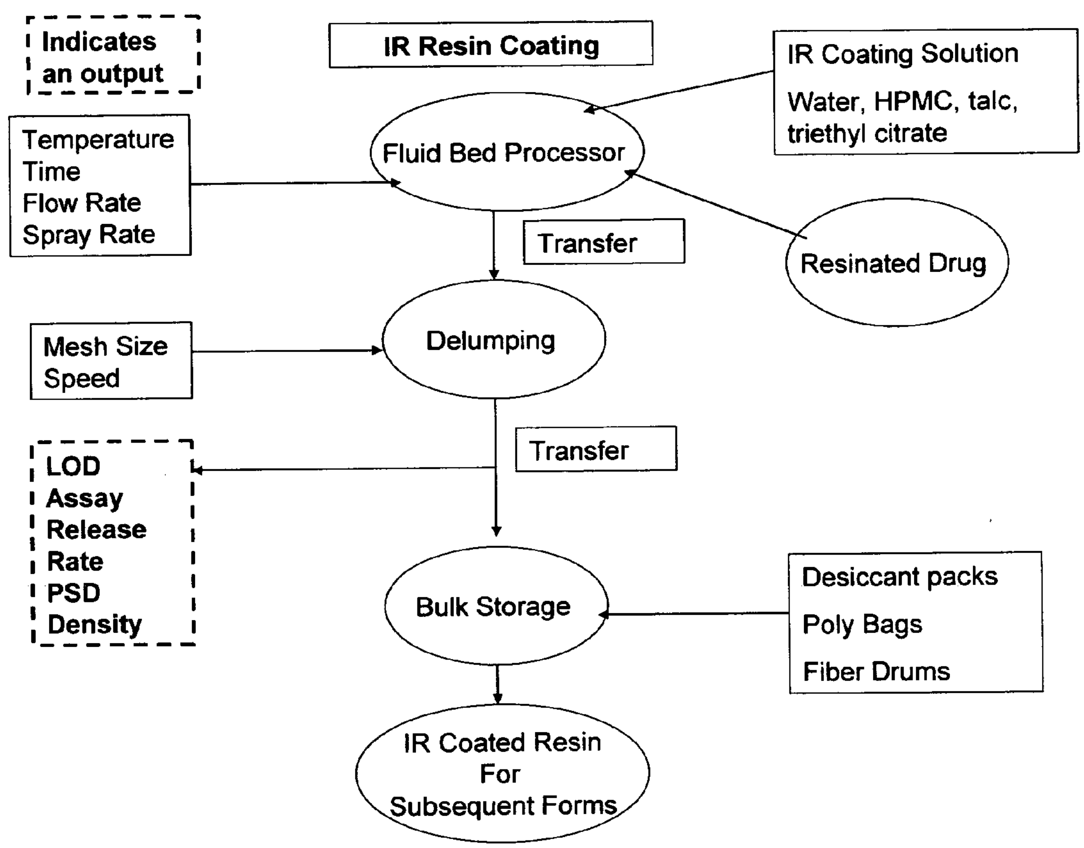
FIG. 4 is a flow chart that illustrates a process for adding an immediate release (IR) resin coating to a drug resinate.

An immediate release (IR) dosage intermediate is prepared having the formulation below by the process illustrated schematically in FIG. 4. The hydrocodone bitartrate content of the dosage is selected to be 5 mg at 55 percent of the saturation concentration (S) in the resinate. The weight of resinate required, R, is determined as follows:

$$0.55\cdot\frac{S}{100}\frac{\text{mg hydrocodone}}{\text{mg resinate}}\times R,\ \text{mg resinate} = 5\ \text{mg hydrocodone}$$

$$\text{Therefore, } R = \frac{100\cdot 5}{0.55\cdot S} = \frac{909.09}{S}\ \text{mg resinate}$$

where S is the saturation concentration of hydrocodone in the resinate as a percent by weight.

As S for hydrocodone bitratrate in IRP 69 is 89.9% then 909.09/89.9=10.112 mg resinate at 55 percent of saturation will contain 10.112 mg×0.55×89.9/100=5 mg hydrocodone bitartrate.

| Component | Amount |
|---|---|
| HCBT*/IRP69 Resinate (See Example 1) | 10.112 mg |
| Magnesium Stearate | 6 mg |
| Colloidal Silicon Dioxide | 6 mg |
| HPMC 6cps | 12 mg |
| Talc | 6 mg |
| Triethyl Citrate | 6 mg |
| Empty Capsule Shell #00 | 118 mg |
| Total IR Component Weight | 164.112 mg |

*5 mg at 55% of saturation concentration in resinate

Example 3

An Immediate Release Resinate Intermediate

Compressed Tablet

| Component | Amount |
|---|---|
| HCBT*/IRP69 Resinate (see Example 1) | 10.112 mg |
| Microcrystalline cellulose | 450 mg |
| Polyplasdone XL | 20 mg |
| HPMC 6cps | 35 mg |
| Anhydrous lactose | 400 mg |
| Magnesium stearate | 6 mg |
| Total Component Weight | 921.112 mg |

*5 mg at 55% of saturation concentration in resinate

Example 4

An Extended Release (ER) Resinate Intermediate for Hard Gelatin Capsules

Figure 5:
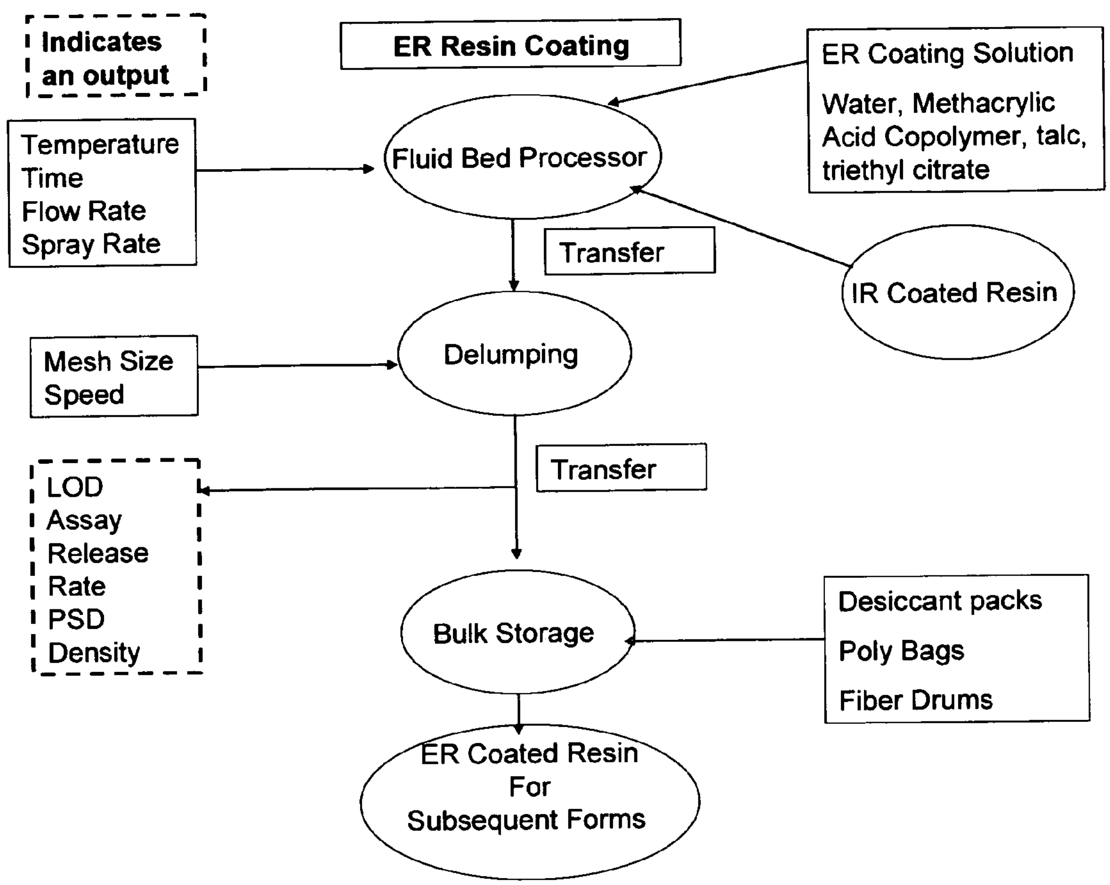
FIG. 5 is a flow chart that illustrates a process for adding an extended release (ER) resin coating to a drug resinate.

An extended release (ER) dosage intermediate is prepared having the formulation below by the process illustrated schematically in FIG. 5.

| Component | Amount |
|---|---|
| HCBT*/IRP69 Resinate (see Example 1) | 20.224 mg |
| Methacrylic Acid Copolymer | 40 mg |
| Talc | 4 mg |
| Triethyl Citrate | 6 mg |
| Colloidal Silicon Dioxide | 6 mg |
| Magnesium Stearate | 5 mg |
| Total Component Weight | 81.224 mg |

*10 mg at 50% of saturation concentration in resinate

Example 5

An Immediate Release Unbound Agent Intermediate

Figure 6:
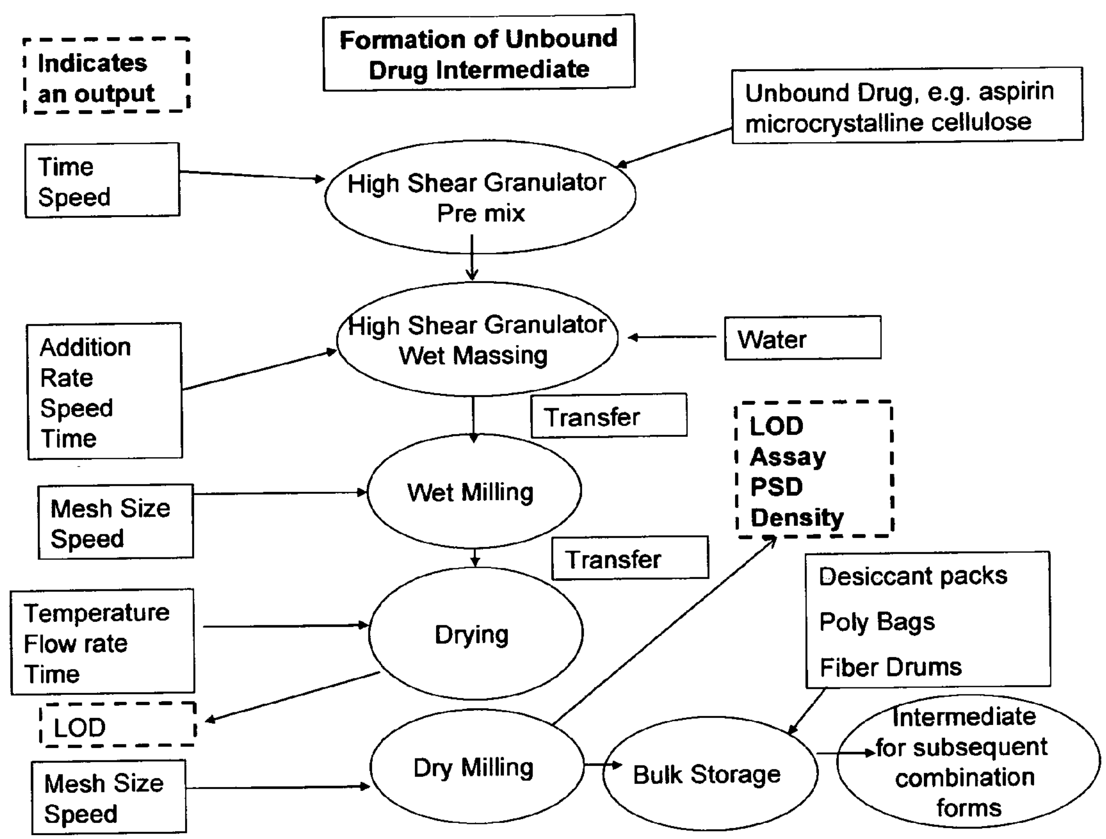
FIG. 6 is a flow chart that illustrates formation of an intermediate composition of an unbound drug.

An immediate release (IR) dosage intermediate of an unbound drug is prepared having the formulation below by the process illustrated schematically in FIG. 6.

| Component | Amount |
|---|---|
| Pseudoephedrine | 30 mg |
| Microcrystalline Cellulose | 425 mg |
| Polyvinylpyrrolidone | 35 mg |
| Magnesium Stearate | 6 mg |
| Colloidal Silicon Dioxide | 6 mg |
| HPMC 6 cps | 5 mg |
| Talc | 4 mg |
| Triethyl Citrate | 2 mg |

Example 6

An Oral Dosage Pharmaceutical Composition of the Invention

Figure 7:
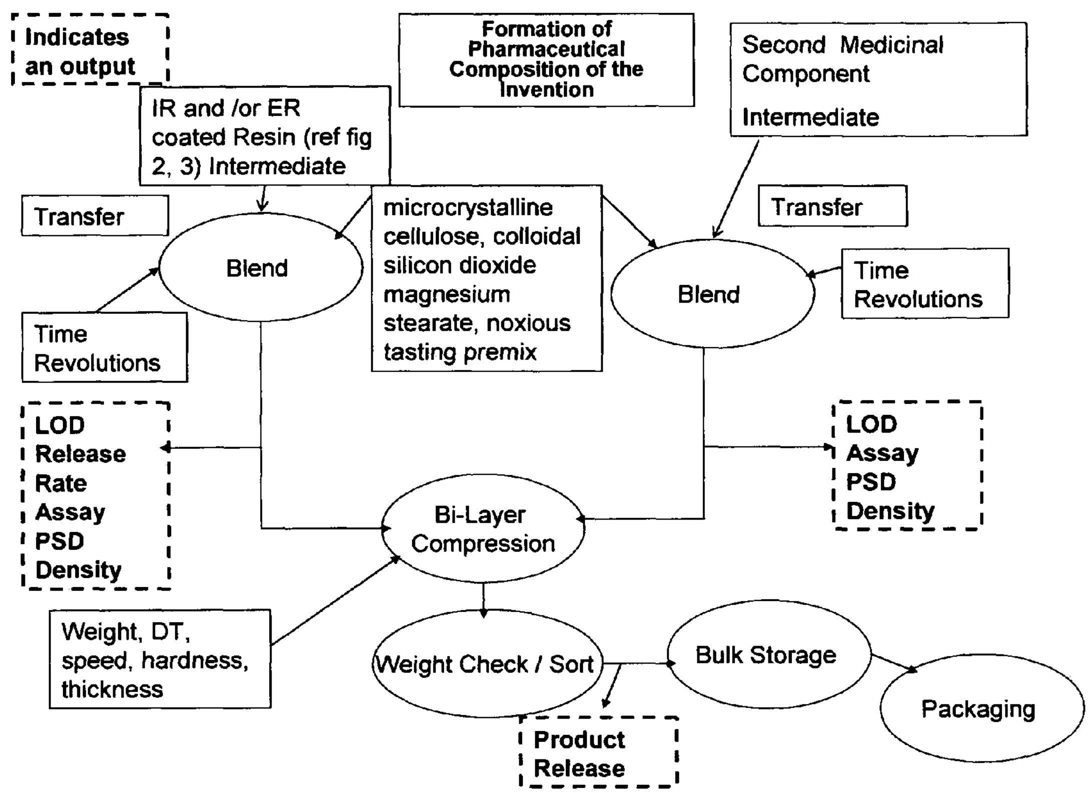
FIG. 7 is a flow chart that illustrates a process for forming an oral dosage pharmaceutical composition of the invention.

An oral dosage pharmaceutical composition of the invention having the formulation below is formed by combining the hydrocodone/IRP69 intermediate described in Example 2 with the unbound aspirin intermediate described in Example 5 by the process illustrated schematically in FIG. 7.

| Component | Amount |
|---|---|
| HCBT*/IRP69 Resinate (see Example 1) | 10.112 |
| Pseudoephedrine | 30 mg |
| Microcrystalline Cellulose | 425 mg |
| Polyvinylpyrrolidone | 35 mg |
| Magnesium Stearate | 6 mg |
| Colloidal Silicon Dioxide | 6 mg |
| Empty Capsule Shell #000 | 163 mg |
| HPMC 6 cps | 5 mg |
| Talc | 4 mg |
| Triethyl Citrate | 2 mg |
| Total Dosage Form Weight | 686.112 mg |

*5 mg at 50% of saturation concentration in resinate

An oral dosage composition of the invention is administered to a patient. The inventive method and composition prevents or minimizes potential inadvertent or intentional overdose events with the drugs therein.

Other Embodiments

All publications, patent applications, and patents mentioned in this specification are herein incorporated by reference.

Various modifications and variations of the described method and system of the invention will be apparent to those skilled in the art without departing from the scope and spirit of the invention. Although the invention has been described in connection with specific desired embodiments, it should be understood that the invention as claimed should not be unduly limited to such specific embodiments. Indeed, various modifications of the described modes for carrying out the invention that are obvious to those skilled in the fields of medicine, immunology, pharmacology, endocrinology, or related fields are intended to be within the scope of the invention.

What is claimed is:

1. A method of treating a patient that prevents or reduces drug abuse and overdose events with drugs, said method comprising: oral administration of a first amount of a pharmaceutical composition comprising at least one drug bound to at least one ion exchange resin as a resinate, said ion exchange resins being selected from the group consisting of a cationic ion exchange resin and a anionic ion exchange resin, each said ion exchange resin being bound to at least one drug, wherein each bound drug, measured as the unbound state, is less than about 75 percent of its saturation concentration in its resinate leaving unused binding capacity in its ion exchange resin, said saturation concentration being defined as the larger of:

(a) the weight of drug per weight of washed and dried resinate after at least three hours of stirred aqueous resination reaction in a slurry of the drug in de-ionized water at a temperature in the range of 59 to 61° C. with the initial weight of drug being at least fourfold that of the weight of ion exchange resin present; and (b) the weight of drug per weight of washed and dried resinate after at least three hours of stirred aqueous resination reaction in a slurry of the drug at a temperature in the range of 59 to 61° C. with the initial weight of drug being at least fourfold that of the weight of ion exchange resin present, and at a pH having a value within about ±1 unit of the $pK_a$ of the drug;

said unused ion exchange binding capacity acting as an ion sink limiting the cumulative release of each bound drug to less than about twice the cumulative release from said first amount if immediately after the administration of said first amount of said pharmaceutical composition, a second equal amount of said pharmaceutical composition is ingested by said patient.

2. The method of treating a patient as described in claim 1, wherein each said bound drug, measured as the unbound state, is less than about 50 percent of its saturation concentration in its resinate.

3. The method of treating a patient as described in claim 1, wherein each said bound drug, measured as the unbound state, is less than about 40 percent of its saturation concentration in its resinate.

4. The method of treating a patient as described in claim 1, wherein each said bound drug, measured as the unbound state, is less than about 30 percent of its saturation concentration in its resinate.

5. The method of treating a patient as described in claim 1, wherein each said bound drug, measured as the unbound state, is less than about 20 percent of its saturation concentration in its resinate.

6. The method of treating a patient as described in claim 1, wherein each said bound drug, measured as the unbound state, is less than about 10 percent of its saturation concentration in its resinate.

7. The method of treating a patient as described in claim 1, wherein each said bound drug, measured as the unbound state, is less than about 5 percent of its saturation concentration in its resinate.

8. The method of treating a patient as described in claim 1, wherein each said bound drug, measured as the unbound state, is less than about 1 percent of its saturation concentration in its resinate.

9. The method of claim 1, wherein said pharmaceutical composition additionally comprises at least one unbound drug, said unbound drug having a complementary therapeutic effect to any said bound drug.

10. The method of claim 9, wherein each said unbound drug has an $LD_{50}$ at least twice as high as any drug bound in a resinate.

11. The method of claim 9, wherein each said unbound drug has an $LD_{50}$ at least three times as high as any drug bound in a resinate.

12. The method of claim 9, wherein each said unbound drug has an $LD_{50}$ at least four times as high as any drug bound in a resinate.

13. The method of claim 9, wherein each said unbound drugs has an $LD_{50}$ at least six times as high as any drug bound in a resinate.

14. The method of claim 9, wherein each said unbound drug has an $LD_{50}$ at least eight times as high as any drug bound in a resinate.

15. The method of claim 9, wherein each said unbound drug has an $LD_{50}$ at least ten times as high as any drug bound in a resinate.

16. The method of claim 1 wherein said pharmaceutical composition comprises warfarin bound to a strong base ion exchange resin as a resinate.

17. The method of claim 1, wherein if immediately after said administration of said first amount of said pharmaceutical composition, a second equal amount is ingested by said patient, said unused ion exchange binding capacity acts as an ion sink to limit the cumulative release of each bound drug to less than about 1.35 times the cumulative release from said first amount.

18. The method of claim 1, wherein if immediately after said administration of said first amount of said pharmaceutical composition, a second amount is ingested by said patient, such that the total amount of said pharmaceutical composition ingested is four times said first amount, said unused ion exchange binding capacity acts as an ion sink to limit the increase in cumulative release of each bound drug to less than about twice the cumulative release from said first amount.

19. The method of claim 1, wherein if immediately after said administration of said first amount of said pharmaceutical composition, a second amount is ingested by said patient such that the total amount of said pharmaceutical composition ingested is eight times said first amount, said unused ion exchange binding capacity acts as an ion sink to limit the increase in cumulative release of each bound drug to less than about six times the cumulative release from said first amount.

20. The method of claim 1, wherein if immediately after said administration of said first amount of said pharmaceutical composition, a second amount is ingested by said patient such that the total amount of said pharmaceutical composition ingested is eight times said first amount, said unused ion exchange binding capacity acts as an ion sink to limit the increase in cumulative release of each bound drug to less than about 2.5 times the cumulative release from said first amount.

* * * * *